(12) United States Patent
Ramin et al.

(10) Patent No.: US 6,210,059 B1
(45) Date of Patent: Apr. 3, 2001

(54) NAIL VARNISH BRUSH AND NAIL VARNISH APPLICATION ASSEMBLY WITH A BRUSH

(75) Inventors: Roland Ramin; Stéphane Lacoutiere, both of Paris (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/449,929

(22) Filed: Nov. 24, 1999

(30) Foreign Application Priority Data

Nov. 27, 1998 (FR) .................................................. 98 14986

(51) Int. Cl.$^7$ ...................................................... A46B 11/00

(52) U.S. Cl. ........................ 401/126; 401/129; 15/207.2; 424/61

(58) Field of Search ................................... 401/126, 129, 401/118, 124; 132/73, 74.5; 424/61; 300/18, 21; 15/159.1, 207.2

(56) References Cited

U.S. PATENT DOCUMENTS

| | | |
|---|---|---|
| 2,665,443 | 1/1954 | Simon et al. . |
| 3,668,170 * | 3/1976 | Maruta et al. ........................ 260/27 |
| 3,779,993 | 12/1973 | Kibler et al. . |
| 3,941,857 * | 3/1976 | Wu ...................................... 260/837 |
| 4,126,144 | 11/1978 | Duarte . |
| 4,158,053 | 6/1979 | Greene et al. . |
| 4,192,649 | 3/1980 | Kato et al. . |
| 4,311,695 | 1/1982 | Starch . |
| 5,354,339 | 10/1994 | Bodnar . |
| 5,357,647 | 10/1994 | Gueret . |
| 5,462,798 | 10/1995 | Gueret . |
| 5,491,865 | 2/1996 | Gueret . |

FOREIGN PATENT DOCUMENTS

| | | |
|---|---|---|
| 0 556 081 | 8/1993 | (EP) . |
| 0 581 922 | 2/1994 | (EP) . |
| 0 648 485 | 4/1995 | (EP) . |

(List continued on next page.)

OTHER PUBLICATIONS

Patent Abstracts of Japan, vol. 098, No. 009, Jul. 31, 1998 (JP 10 110387).

Derwent Publications Ltd., London, GB, AN 88165901 (JP 53 105189).

(List continued on next page.)

*Primary Examiner*—David J. Walczak
(74) *Attorney, Agent, or Firm*—Finnegan, Henderson, Farabow, Garrett & Dunner, L.L.P.

(57) ABSTRACT

A method of treating the bristles of a tuft of bristles of the brush, nail varnish application assembly requiring such a brush, and a brush for the application of a make-up or beauty product, having a tuft (2) of approximately parallel bristles (3), a first end of these bristles (3) being fastened to a free end (4a) of a wand (4), the bristles (3) of the tuft (2) being surface-impregnated with a partially acetylated polyvinyl alcohol comprising at least units of formulae (I) and (II):

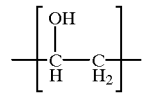

(I)

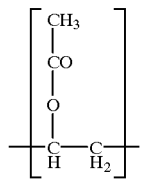

(II)

in which the units of formulae (II) are present in proportions ranging from 3 mol % to 40 mol % with respect to the polymer, the polyvinyl alcohol having a weight-average molecular weight ranging from 10,000 to 190,000.

35 Claims, 1 Drawing Sheet

FOREIGN PATENT DOCUMENTS

| | | |
|---|---|---|
| 0 651 955 | 5/1995 | (EP) . |
| 0 673 612 | 9/1995 | (EP) . |
| 0 680 742 | 11/1995 | (EP) . |
| 2 685 925 | 7/1993 | (FR) . |
| 2 755 009 | 4/1998 | (FR) . |
| 0 568 150 | 3/1945 | (GB) . |
| WO 97/22666 | 6/1997 | (WO) . |
| WO 97/42930 | 11/1997 | (WO) . |

OTHER PUBLICATIONS

English language Derwent Abstract of EP 0 581 922.
English language Derwent Abstract of EP 0 648 485.
English language Derwent Abstract of EP 0 651 955.
English language Derwent Abstract of EP 0 673 612.
English language Derwent Abstract of EP 0 680 742.
English language abstract of FR 2 755 009.

* cited by examiner

NAIL VARNISH BRUSH AND NAIL VARNISH APPLICATION ASSEMBLY WITH A BRUSH

The present invention relates to a brush for the application of a make-up or beauty product, such as a nail varnish or a nail care product, a liquid lip product or a liquid foundation, of the kind comprising bristles which are arranged approximately parallel to each other in a tuft and are fastened to a support called a brush wand.

Nail varnishes are generally packaged in an application assembly comprising a container provided with a neck and with a stopper, wherein the stopper is integral with an applicator brush immersed, in a storage position, in the nail varnish product contained in the container.

For proper application of the nail varnish, it is important for the tuft of bristles of the brush to be uniform so as to deposit a uniform layer of varnish on the nails. However, during transportation and storage of the brush before it is packaged with the container containing the varnish product, the tuft of bristles may be deformed, for example, by one or more bristles of the tuft becoming bent or curved; the bristles are then splayed and no longer form a uniform tuft. Such a deformed tuft does not allow the product to be uniformly applied to the nails. In addition, the brush is difficult to introduce through the neck of the container, thus disturbing the proper execution of the industrial process of packaging the varnish.

To avoid deformation of the tuft of bristles, it is possible to treat the tuft of bristles, before it is packaged in the container, by impregnating it with a solution of a film-forming polymer, called a reinforcing solution. After drying, a coating of the film-forming polymer forms on the surface of the bristles, preventing the latter from becoming deformed or splayed; the bristles are thus reinforced.

The reinforcing solution must be sufficiently fluid to allow rapid impregnation of the tuft of bristles. The solution must be capable of impregnating, by capillary effect, enough of the tuft to ensure proper retention of the tuft. After being deposited on the tuft, the solution must dry rapidly in order to leave on the tuft a polymer coating that is not tacky, does not crumble and is flexible and unbrittle. The polymer coating must be able to dissolve rapidly when the tuft is immersed in the nail varnish product without disturbing the cosmetic properties of the product, or destabilizing it.

Nitrocellulose is one of the film-forming polymers most commonly used in nail varnishes in an organic solvent medium. For such varnishes, the reinforcing solution is a solution of nitrocellulose and a plasticizing agent. Nail varnishes in an aqueous medium comprising particles of film-forming polymers dispersed in the aqueous medium are also known, as described, for example, in European patent application EP-A-648,485; in these products, the film-forming polymer in the dispersed particle state is insoluble in water. To treat brushes intended for applying a water-based varnish, an aqueous solution containing a water-soluble polymer can be used as a reinforcing solution. This water-soluble polymer has a different nature from the water-insoluble film-forming polymer present in the varnish product. Unlike varnishes in a solvent medium comprising nitrocellulose, it is difficult to treat the tuft of the brush with the same film-forming polymer present in the varnish product.

An object of the present invention is, therefore, to provide a reinforced brush suitable for applying nail varnishes in an aqueous medium.

Surprisingly, the inventors have found that such a brush can be obtained by employing a particular polyvinyl alcohol to reinforce the tuft of bristles. This polymer is readily dissolved in water and makes it possible to obtain a fluid aqueous solution allowing the tuft to be rapidly impregnated; the aqueous solution deposited on the tuft dries rapidly and leaves a coating on the bristles that is not tacky and does not crumble. The bristles thus treated remain sufficiently flexible, while not splaying, and form a homogeneous tuft, even after the constraints of transporting and storing the brush before packaging it. Furthermore, after the brush has been fitted into the varnish container, the polymer coating rapidly dissolves in the varnish product containing water, without modifying the cosmetic properties of the varnish, or destabilizing the product.

Specifically, a subject of the invention is a brush for the application of a make-up or beauty product, comprising a tuft of bristles provided on a wand, characterized in that the bristles of the tuft are surface-impregnated with a partially acetylated polyvinyl alcohol comprising at least units of formulae (I) and (II):

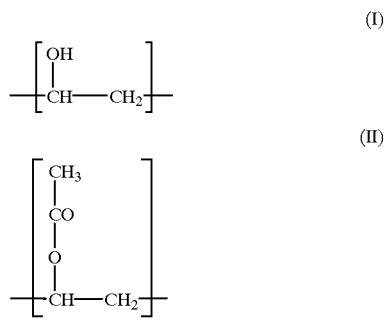

in which the units of formula (II) are present in proportions ranging from 3 mol % to 40 mol % with respect to the polymer, the polyvinyl alcohol having a weight average molecular weight ranging from 10,000 to 190,000. In an embodiment of the invention, the bristles are approximately parallel and are fastened to the wand.

Another subject of the invention is a method of coating bristles of a tuft of a brush, for the application of a make-up product, comprising a tuft of bristles provided on a wand, characterized in that at least part of the tuft of bristles is brought into contact with an aqueous composition comprising a polyvinyl alcohol as defined above, the tuft of bristles is then removed from the composition and left to dry.

Another subject of the invention is a brush for the application of a make-up product capable of being obtained according to the method defined above.

Yet another subject of the invention is an application assembly for a nail varnish or nail care product, comprising a container provided with a neck and with a stopper integral with a brush, as defined above, which is immersed, in a storage position, in a nail varnish or nail care product including an aqueous medium contained in this container.

Still another subject of the invention is an application assembly for a nail varnish or nail care product, comprising a container provided with a neck and with a stopper integral with a brush immersed, in a storage position, in a nail varnish or nail care product contained in the container, wherein the product includes an aqueous medium containing at least one polyvinyl alcohol as defined above.

The polyvinyl alcohol used according to the invention has a weight-average molecular weight ranging from 10,000 to 190,000, preferably from 10,000 to 120,000, and even more preferably from 31,000 to 50,000, so as to obtain a reinforcing solution sufficiently fluid to be able to impregnate the tuft of bristles of the brush by capillary effect.

Advantageously, the units of formula (II) may be present in the polyvinyl alcohol in a proportion ranging from 10 to 15 mol %.

In a preferred embodiment of the invention, the polyvinyl alcohol consists essentially of units of formulae (I) and (II).

Usable polyvinyl alcohols according to the invention include those sold under the names "AIRVOL 203", "AIRVOL 205", "AIRVOL 6108", "AIRVOL 523" AND "AIRVOL 540" by Air Products Chemical, "RHODOVIOL 4/125", "RHODOVIOL 14/135" and "RHODOVIOL 25/140" by Rhône-Poulenc, "MOWIOL 4-88", "MOWIOL 40-88" and "MOWIOL 18-88" by Hoechst, and "ELVANOL 51-05" and "ELVANOL 52-22" by DuPont.

The bristles of the tuft may be made of a material chosen from polyamides, polyesters, polyether-block amides, polyethylene, polytetrafluoroethylene, polyvinylidene fluoride, polyvinyl chlorides, viscose, rayon, polyacetals, natural silks, and blends thereof.

The bristles making up the brush may, preferably, have a cross section inscribed in a circle ($\phi$) of diameter ranging, for example, from $4/100$ to $40/100$ of a millimeter.

According to an alternative embodiment of the invention, the tuft may comprise a blend of small cross-sectional bristles, or fine bristles, and of larger cross-sectional bristles, or coarse bristles, the proportion of coarse bristles possibly ranging from 2% to 95%, and preferably from 10% to 90%, by volume with respect to the total volume of the tuft of the brush. In particular, the fine bristles may have an inscribed cross section ranging from $4/100$ to $10/100$ of a millimeter and the coarse bristles may have an inscribed cross section ranging from $11/100$ to $40/100$ of a millimeter.

Advantageously, the tuft of bristles of the brush may have a length ranging from 5 to 25 mm and, preferably, a length ranging from 13 to 20 mm.

According to a beneficial aspect of the invention, the bristles may have a first end obtained by bending a bundle of fibers into a U, the base of the U being retained, by a pushed-in fastener, in a housing made in the free end of the wand of the brush. Advantageously, this housing may be a cylinder of revolution. It may also have an oval, elongate or cruciform shape or be in the form of a half-round tile. This housing may be flared towards the free end of the wand. The tuft of bristles may also be fixed in this housing by adhesive bonding or by any other means normally used for the manufacture of brushes, for example, by means of a ferrule.

The number of bristles making up the tuft may advantageously range from 100 to 600.

The material of which the bristles are composed may advantageously contain an agent that modifies their surface state and/or their slip characteristics and/or that reduces their wettability with respect to the water and/or to the solvent contained in the make-up product, and, especially, in the varnish, or an antistatic agent.

Advantageously, the agent improving the slip characteristic of the bristles and reducing their wettability with respect to water may be incorporated in the material of the bristles in an amount ranging from 0.2% to 15% by weight.

This slip agent may, preferably, be chosen from polytetrafluoroethylene, boron nitride, molybdenum disulphide, graphite, silicones, fullerines and talc.

Advantageously, at least some of the bristles may have slight corrugations on their length. The bristles may have cross sections whose shape is chosen from circular, polygonal, annular, cruciform, rectangular, multilobate, U, C and V shapes and of shapes having at least one capillary groove.

The free end of the bristles making up the brush may be made in the form of a pin head, especially obtained by heat treatment, for example, by flame brushing. The free end of the bristles may also be tapered, this tapering being obtained, for example, by grinding or by carding.

The cross section of the brush may have various shapes; in particular, the tuft may have a circular cross section, a section in the form of a half-round tile or an oval or cruciform cross section. Moreover, the bristles may have different lengths. In addition, the free end of the brush may be flat or rounded.

Usable brushes according to the invention are particularly described in European patent applications EP-A-556,081, EP-A-581,922, EP-A-651,955 and EP-A-673,612, the full disclosure of which are incorporated herein by reference.

To obtain the brush according to the invention, at least part, or even all, of the tuft of bristles of the brush are brought into contact with an aqueous composition comprising the polyvinyl alcohol as defined above. Advantageously, half the length of the tuft of bristles may be immersed in the composition; the end of the tuft may also be just touching the composition for a time sufficient for the tuft to be impregnated by capillary effect. The contact time may be relatively short, and, especially, less than or equal to 5 seconds; a momentary dipping operation may also be carried out.

Since polyvinyl alcohol completely dissolves in water, the aqueous composition used in the method according to the invention, the so-called reinforcing solution, is present in the form of an aqueous solution of the polyvinyl alcohol.

Preferably, the polyvinyl alcohol is present in the composition in an amount ranging from 0.1% to 10% by weight, and more preferably from 0.5 to 5% by weight with respect to the total weight of the composition to make it possible to obtain a very fluid solution conducive to good impregnation of the tuft of bristles.

After the brush has been impregnated, it is removed from the reinforcing solution and then left to dry until the polymer coating deposited on the bristles is dry. The drying may be carried out in ambient air or using a heat source or blown air, e.g., a fan.

To reduce the drying time of the reinforcing solution after the tuft has been impregnated, the reinforcing solution may furthermore include at least one $C_2$–$C_5$ lower alcohol, in particular, ethanol. The content of lower alcohol in the composition may range from 0% to 80% by weight and, preferably, ranges from 40% to 70% by weight with respect to the total weight of the composition.

The reinforcing solution may furthermore include a wetting agent to reduce the surface tension of the solution and to promote good impregnation of the bristles of the brush. As a wetting agent, a dimethicone copolyol may, for example, be employed. The wetting agent may be present in an amount ranging from 0.1 % to 15% by weight and, preferably, from 0.5% to 5% by weight with respect to the total weight of polyvinyl alcohol.

The dimethicone copolyol may be chosen from compounds of general formula (III):

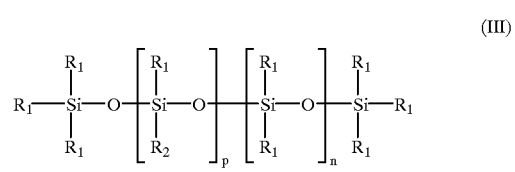

in which formula:

$R_1$, which are identical or different, represent a hydrogen atom, a linear or branched $C_1$–$C_{30}$ alkyl radical, or a phenyl radical;

$R_2$, which are identical or different, represent
—$(C_xH_{2x})$—$(OC_2H_4)_a$—$(OC_3H_6)_b$—$OR_3$;

$R_3$, which are identical or different, are chosen from a hydrogen atom, a linear or branched alkyl radical having from 1to 12 carbon atoms, and a linear or branched acyl radical having from 2 to 12 carbon atoms;

n varies from 0 to 1000;

p varies from 1 to 30;

a varies from 0 to 50;

b varies from 0 to 50;

a+b is greater than or equal to 1;

x varies from 1 to 5; and the number-average molecular weight being greater than or equal to 15,000 and, preferably, lying between 25,000 and 75,000.

Preferably, the oxyalkylenated silicones of general formula (III) used meet at least one, and preferably all, of the following conditions:

$R_1$ denotes a methyl radical;

$R_3$ represents a hydrogen atom, a methyl radical or an acetyl radical, and, preferably, hydrogen;

p varies from 8 to 20;

a lies between 5 and 40 and, preferably, between 15 and 30;

b lies between 5 an 40 and, preferably, between 15 and 30;

x is equal to 2or3;

n varies from 20 to 600, preferably from 50 to 500 and, even more preferably from 100 to 300.

Such silicones are described, for example, in U.S. Pat. No. 4,311,695, the disclosure of which is incorporated herein by reference.

Dimethicone copolyols were, in particular, presented by Dow Corning during the 17th International Congress of the IFSCC in October 1992 and reported in the article "Water-soluble dimethicone copolyol waxes for the personal care industry" by Linda Madore et al., at pages 1 to 3.

These dimethicone copolyols are polydimethylsiloxanes (PDMS) containing one or more water-soluble ether functional groups (oxyalkylenes, especially oxyethylene and/or oxypropylene).

Such dimethicone copolyols are sold by Goldschmidt under the name ABIL B8851 or ABIL B88183. Other examples include the compounds KF 351 to 354 and KF 615 A, sold by Shin-Etsu or DMC 6038 from Wacker.

The dimethicone copolyol derivatives that can be used may, in particular, be dimethicone copolyols having a phosphate group, a sulphate group, a polydimethylammonium myristamide chloride group, a stearate group, an amine group, which is glyco-modified, etc. It is possible to use as dimethicone copolyol derivatives the compounds sold by Siltech under the name Silphos A100, Siltech amine 65, Silwax WDIS, and myristamido silicone quat, or by Phoenix under the name Pecosil PS 100.

It is also possible to use the derivatives sold by Wacker under the name VP 1661, or by Dow Corning under the name 2501 Cosmetic Wax. It is additionally possible to use the derivatives sold by Wacker under the name VP 1661, or by Dow Corning under the name 2501 Cosmetic Wax.

The silicones most particular preferred are, for example, those sold by Dow Corning under the brand name Q2-5220 and by Rhône-Poulenc under the name MIRASIL DMCO.

The brush according to the invention is particularly suitable for the packaging and application of a nail varnish or nail care product comprising an aqueous medium. The nail varnish or nail care application assembly comprises a container provided with a neck and with a stopper integral with a brush as defined above, the brush being immersed, in a storage position, in a nail varnish or nail care product including an aqueous medium contained in this container.

After the brush has been fitted into the container, the polyvinyl alcohol present on the surface of the bristles of the brush easily dissolves in the aqueous nail varnish or nail care product. This product thus packaged with the application assembly therefore contains, in the aqueous medium, dissolved polyvinyl alcohol, which may be present in an amount ranging from 0.005 to 0.5% by weight with respect to the total weight of the product.

Cosmetic nail varnish or nail care products generally include at least one water-insoluble film-forming polymer in the form of particles dispersed in the aqueous medium. Since this film-forming polymer is insoluble in water, it, therefore, has a different chemical nature from the water-soluble polyvinyl alcohol employed for treating the brush defined above.

As film-forming polymer, it is possible to use, in a known manner, synthetic, radical-type or polycondensation-type polymers, polymers of natural origin, and blends thereof.

The expression "radical film-forming polymer" should be understood to mean a polymer obtained by the polymerization of unsaturated, especially ethylenically unsaturated, monomers, each monomer being capable of being homopolymerized (unlike polycondensation products).

Examples of radical-type film-forming polymers include vinyl polymers and copolymers, especially acrylic polymers.

The vinyl film-forming polymers may result from the polymerization of ethylenically unsaturated monomers having at least one acid group and/or of the esters of these acid monomers and/or of the amides of these acid monomers.

It is possible to use, as monomers carrying an acid group, α, or β-ethylenically unsaturated carboxylic acids, such as acrylic acid, methacrylic acid, crotonic acid, maleic acid and itaconic acid.

The esters of acid monomers may be chosen from the esters of (meth)acrylic acid (also called (meth)acrylates), especially alkyl, particularly $C_1$–$C_{20}$ alkyl, (meth)acrylates, aryl, particularly $C_6$–$C_{10}$ aryl, (meth)acrylates and hydroxyalkyl, particularly $C_2$–$C_6$ hydroxyalkyl, (meth)acrylates.

Examples of amides of acid monomers include, for example, (meth)acrylamides, and especially N-alkyl, particularly $C_2$–$C_{12}$ alkyl (meth)acrylamides.

The film-forming vinyl polymers may also result from the homopolymerization or copolymerization of monomers chosen from vinyl esters and styrene monomers. In particular, these monomers may be polymerized with acid monomers and/or their esters and/or their amides, such as those mentioned above.

Examples of vinyl esters include vinyl acetate, vinyl neodecanoate, vinyl pivalate, vinyl benzoate and vinyl t-butylbenzoate.

Examples of styrene monomers include styrene and alpha-methyl styrene.

The list of monomers given is not exhaustive, and it is possible to use any monomer known to those skilled in the art falling within the categories of acrylic monomers and vinyl monomers, including monomers modified by a silicone chain.

Radical polymers that can be used in nail varnish or nail care products are described in U.S. Pat. No. 4,158,053, PCT Publication No. WO-A-97/42930 and French Application No. FR-A-2,755,009, the disclosures of which are incorporated herein by reference.

Examples of polycondensation products that can be used as film-forming polymers include anionic, cationic, nonionic or amphoteric polyurethanes, acrylic polyurethanes, polyvinylpyrrolidone-polyurethanes, polyester-polyurethanes, polyether-polyurethanes, polyureas, polyurea-polyurethanes, and blends thereof. Polyurethanes that can be used are described in European patent application EP-A-680,742, the disclosure of which is incorporated herein by reference.

Examples of polycondensation products that can be used as the film-forming polymer include polyesters, polyesteramides, polyesters having a chain, polyamides and epoxy ester resins. Polyesters that can be used are described in U.S. Pat. No. 3,779,993, or those sold under the name Eastman AQ® by Eastman Chemical can be used.

The polymers of natural origin, optionally modified, may be chosen from shellac resin, gum sandarac, dammars, gum elemi, copals, water-insoluble cellulose polymers, and blends thereof. Such polymers are described in European patent application EP-A-676,451, the disclosure of which is incorporated herein by reference.

The dispersion comprising one or more film-forming polymers may be prepared by those skilled in the art on the basis of their general knowledge.

The size of the polymer particles in aqueous dispersion may range from 10 to 500 nm and, preferably, range from 20 to 300 nm.

The polymer in aqueous dispersion may be present in the nail varnish or nail care product in an amount ranging from 1% to 50%, and, preferably, from 5% to 45%, by weight of dry matter of film-forming polymers with respect to the total weight of the product.

The nail varnish or nail care product may contain plasticizers and/or coalescing agents well known to those skilled in the art.

The invention comprises, apart from the arrangements mentioned above, a certain number of other arrangements, which will be more fully explained below by entirely non-limiting illustrative embodiments, described with reference to the appended drawings. These embodiments are designed to teach those of ordinary skill in the art how to practice the invention and should not be construed as limiting the invention as claimed.

Figure 1:
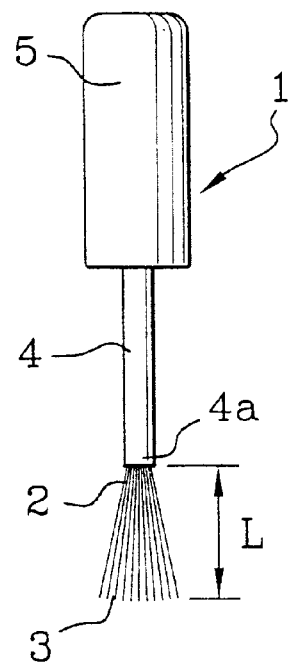
FIG. 1 is a side view of a nail varnish brush according to the invention.

FIG. 1 shows a brush 1 for the application of nail varnish, comprising a tuft 2 of bristles 3 fastened at one end 4$a$ of a wand 4 and oriented approximately in the axial direction of the wand. A sleeve 5 is provided on an end of the wand 4 opposite from the tuft 2. In a preferred embodiment, the end of the wand 4 is fitted into the sleeve 5, and the sleeve 5 is cylindrical. The sleeve 5 preferably serves as a member for handling the brush. It also preferably serves as a stopper intended, for example, to be screwed onto the neck of a varnish bottle. The tuft 2 is preferably obtained from a bundle of approximately parallel bristles folded in two, approximately, halfway along their length. The tuft 2 is preferably fastened, in a known manner, to the end 4$a$ of the wand 4 for example, by fitting the folded part of the tuft of bristles into a housing, formed by a blind hole opening at the end of the wand 4. Reference may be made to European patent applications EP-A-651,955 and EP-A-673,612, the disclosures of which are incorporated herein by reference, for a detailed description of the fastening of the tuft of bristles to the wand.

Figure 2:
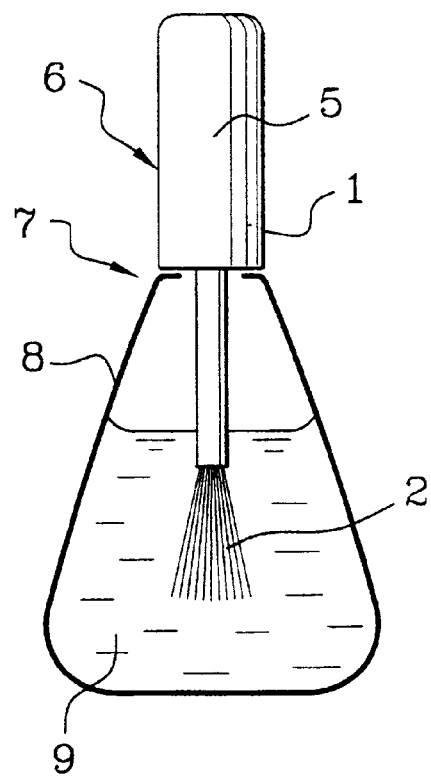
FIG. 2 is a side view of a nail varnish assembly according to the invention.

FIG. 2 shows a nail varnish assembly 6 comprising the brush 1 of FIG. 1 placed on the neck 7 of a bottle 8 containing a nail varnish product 9 which includes water, the tuft 2 of bristles being immersed in the product 9. The product 9 includes the polyvinyl alcohol according to the invention dissolved in the aqueous medium; it furthermore includes a water-insoluble film-forming polymer in the form of particles dispersed in the aqueous medium.

An example of brush treatment according to the method of the invention, and comparative examples made using a method not forming part of the invention, will be given below. The following examples are merely illustrative of the invention and should not be construed as limiting the invention as claimed.

EXAMPLE 1

A reinforcing solution S1 was prepared with the following composition:

| Solution 1: | |
| --- | --- |
| partially acetylated polyvinyl alcohol (AIRVOL 205 from Air Product Chemical) | 1.5 g |
| ethyl alcohol | 66 g |
| water, qs | 100 g. |

A brush having the following characteristics was treated with this solution:

exposed length of the bristles: 18 mm

90% cylindrical bristles made of nylon-11 (RILSAN), 15/100 mm, filled with 5% molybdenum disulphide, approximately 110 bristles;

b 10% cylindrical bristles made of nylon-6,12 (TYNEX nylon), 8/100 mm, approximately 46 bristles.

The tuft of the brush was dipped halfway into the solution for one second.

The brush was then removed and left to dry in the air. After drying, the polyvinyl alcohol coating the surface of the bristles was not tacky and gave the bristles good flexibility while still keeping them in a uniform tuft.

During immersion of the brush in an aqueous nail varnish product, for example, one identical to those of the examples in European patent application EP-A-648,485, the disclosure of which is incorporated herein by reference, the polymer on the surface of the bristles dissolved very readily in the aqueous medium and did not modify the cosmetic properties of the varnish. The homogeneous tuft of the brush allowed a uniform layer of the varnish to be applied to one's nail.

The brush of Example 1 was placed in a bottle containing the following nail varnish product:

| | |
| --- | --- |
| aqueous polyester-polyurethane dispersion with a 35% solids content (AVALURE UR 405 from Goodrich) | 25 g MA |
| acetyle tributylcitrate | 2.5 g |
| ethanol | 5 g |
| clay | 1 g |

-continued

| | |
|---|---|
| pigments | 3 g |
| preservatives | qs |
| water | qs 100 g. |

After the tuft of the brush had been immersed in the nail varnish product, the polyvinyl alcohol completely dissolved in the varnish. The latter was not destabilized and retained its cosmetic properties.

EXAMPLE 2

The same procedure described in Example 1 was carried out using the following reinforcing solution 2:

| Solution 2: | |
|---|---|
| partially acetylated polyvinyl alcohol (AIRVOL 540 from Air Product Chemical) | 1.7 g |
| ethanol | 50 g |
| water | qs 100 g. |

After the tuft of the brush had been immersed in the nail varnish product, the polyvinyl alcohol completely dissolved in the varnish. The latter was not destabilized and retained its cosmetic properties.

COMPARATIVE EXAMPLES 3 AND 4

Two reinforcing solutions not forming part of the invention, were produced with the following compositions:

| Solution 3: | |
|---|---|
| sodium polymethacrylate (DARVAN 7 from Vanderbilt) | 2.5 g |
| ethanol | 20 g |
| water | qs 100 g. |

| Solution 4: | |
|---|---|
| hydroxypropyl methyl cellulose (METHOCEL E4 M UG from Dow Chemical) | 0.67 g |
| ethanol | 66.6 g |
| water | qs 100 g. |

For each solution, a brush having the same characteristics as that of Example 1 was treated by dipping it halfway into the solution for 1 second.

It was found that treatment with Solution 3 did not allow the impregnated tuft of bristles to dry rapidly since the tuft was not dry to touch after 30 minutes. This excessively long drying time was not suitable for industrial implementation of the treatment of the brush.

Solution 4 resulted, after dipping and drying, in the formation of a hard film. In addition, the film easily fractured when subjected to a slight impact, for example, by twisting the tuft, and it followed that the bristles were no longer reinforced and the tuft could then be easily deformed.

Only a brush treated according to Example 1 or 2 of the invention made it possible to achieve good reinforcement of the tuft as well as proper dissolution of the polyvinyl alcohol in the aqueous varnish product without impairing the stability or the cosmetic properties of the varnish.

The foregoing written description relates to various embodiments of the present invention. Numerous changes and modifications may be made therein without departing from the spirit and scope of the invention as defined in the following claims.

What is claimed is:

1. A brush for the application of a make-up or beauty product, said brush comprising: a wand and a tuft of bristles provided on said wand, wherein said bristles of said tuft are surface-impregnated for the purpose of reinforcing said bristles with a sufficient amount of at least one partially acetylated polyvinyl alcohol comprising at least units of formulae (I) and (II):

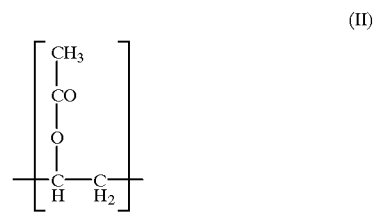

in which said units of formula (II) are present in a proportion ranging from 3 mol % to 40 mol % with respect to the polymer, said polyvinyl alcohol having a weight-average molecular weight ranging from 10,000 to 190,000.

2. A brush according to claim 1, wherein said polyvinyl alcohol has a weight-average molecular weight ranging from 10,000 to 120,000.

3. A brush according to claim 2, wherein said polyvinyl alcohol has a weight-average molecular weight ranging from 31,000 to 50,000.

4. A brush according to claim 1, wherein said units of formula (II) are present in a proportion ranging from 10 to 15 mol %.

5. A brush according to claim 1, wherein said polyvinyl alcohol consists essentially of units of formulae (I) and (II).

6. A brush according to claim 1, wherein said bristles are made of a material chosen from polyamides, polyesters, polyether-block amides, polyethylene, polytetrafluoroethylene, polyvinylidene fluoride, polyvinyl chlorides, viscose, rayon, polyacetals, natural silks, and blends thereof.

7. A brush according to claim 1, wherein said bristles have a cross section inscribed in a circle of diameter ranging from $4/100$ to $49/1000$ of a millimeter.

8. A brush according to claim 1, wherein said tuft of said bristles has a length ranging from 5 to 25 millimeters.

9. A brush according to claim 1, having a number of bristles making up said tuft, wherein said number of bristles ranges from 100 to 600.

10. A nail varnish brush comprising a brush according to claim 1.

11. A method of coating bristles of a brush, wherein said brush comprises a tuft of bristles provided on a wand, said method comprising:

contacting at least part of said tuft of bristles with an aqueous composition of a partially acetylated polyvinyl alcohol, wherein said composition comprises at least units of formulae (I) and (II):

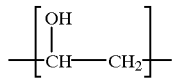

(I)

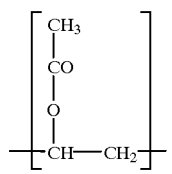

(II)

in which said units of formula (II) are present in a proportion ranging from 3 mol % to 40 mol % with respect to the polymer, said polyvinyl alcohol having a weight-average molecular weight ranging from 10,000 to 190,000;

removing said tuft of bristles from said composition; and drying said tuft of bristles.

12. A method according to claim 11, wherein said polyvinyl alcohol has a weight-average molecular weight ranging from 10,000 to 120,000.

13. A method according to claim 12, wherein said polyvinyl alcohol has a weight-average molecular weight ranging from 31,000 to 50,000.

14. A method according to claim 11, wherein said units of formula (II) are present in a proportion ranging from 10 to 15 mol %.

15. A method according to claim 11, wherein said polyvinyl alcohol is present in the composition in an amount ranging from 0.1% to 10% by weight with respect to the total weight of the composition.

16. A method according to claim 15, wherein said polyvinyl alcohol is present in the composition in an amount ranging from 0.5% to 5% by weight with respect to the total weight of the composition.

17. A method according to claim 11, wherein said composition further comprises at least one $C_2$–$C_5$ lower alcohol.

18. A method according to claim 17, wherein said at least one lower alcohol is ethanol.

19. A method according to claim 17, wherein said at least one $C_2$–$C_5$ lower alcohol is present in an amount up to 80% by weight with respect to the total weight of the composition.

20. A method according to claim 19, wherein said at least one $C_2$–$C_5$ lower alcohol is present in an amount ranging from 40% to 70% by weight with respect to the total weight of the composition.

21. A method according to claim 11, wherein said composition further comprises a wetting agent.

22. A method according to claim 21, wherein said wetting agent is a dimethicone copolyol.

23. A method of making a brush, said method comprising:

fastening a tuft bristles to a wand;

contacting at least part of said tuft of bristles with an aqueous composition of a partially acetylated polyvinyl alcohol, wherein said composition comprises at least units of formulae (I) and (II):

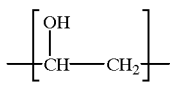

(I)

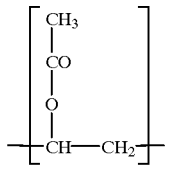

(II)

in which said units of formula (II) are present in a proportion ranging from 3 mol % to 40 mol % with respect to the polymer, said polyvinyl alcohol having a weight-average molecular weight ranging from 10,000 to 190,000;

removing said tuft of bristles from said composition; and drying said tuft of bristles.

24. An application assembly for a nail varnish or nail care product, said assembly comprising a container provided with a neck and with a stopper integral with a brush immersed, in a storage position, in a nail varnish or nail care product contained in said container, wherein said nail varnish or nail care product includes an aqueous medium, wherein said brush comprises a tuft of bristles, said bristles being provided on a wand, and wherein said brush is made by a method comprising:

contacting at least part of said tuft of bristles with an aqueous composition of a partially acetylated polyvinyl alcohol, wherein said composition comprises at least units of formulae (I) and (II):

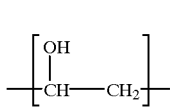

(I)

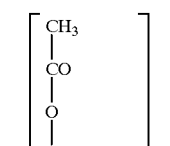

(II)

in which said units of formula (II) are present in a proportion ranging from 3 mol % to 40 mol % with respect to the polymer, said polyvinyl alcohol having a weight-average molecular weight ranging from 10,000 to 190,000;

removing said tuft of bristles from said composition; and drying said tuft of bristles.

25. An application assembly for a nail varnish or nail care product, comprising a container provided with a neck and with a stopper integral with a brush which is immersed in a nail varnish or nail care product contained in said container, wherein said nail varnish or nail care product includes an aqueous medium containing at least one partially acetylated polyvinyl alcohol comprising at least units of formulae (I) and (II):

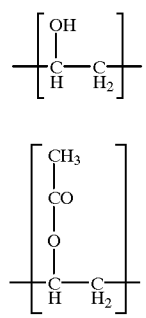

in which said units of formula (II) are present in a proportion ranging from 3 mol % to 40 mol % with respect to the polymer, said polyvinyl alcohol having a weight-average molecular weight ranging from 10,000 to 190,000, and wherein said brush is surface-impregnated with a sufficient amount of said at least one partially acetylated polyvinyl alcohol for the purpose of reinforcing said brush prior to immersion in said nail varnish or said nail care product.

26. An assembly according to claim 25, wherein said polyvinyl alcohol has a weight-average molecular weight ranging from 10,000 to 120,000.

27. An assembly according to claim 26, wherein said polyvinyl alcohol has a weight-average molecular weight ranging from 31,000 to 50,000.

28. An assembly according to claim 25, wherein said units of formula (II) are present in a proportion ranging from 10 to 15 mol % with respect to the polymer.

29. An assembly according to claim 25, wherein said polyvinyl alcohol consists essentially of units of formulae (I) and (II).

30. An assembly according to claim 25, wherein said polyvinyl alcohol is present in the product in an amount ranging from 0.005% to 0.5% by weight with respect to the total weight of the nail varnish or nail care product.

31. An assembly according to claim 25, wherein said nail varnish or nail care product further comprises a water-insoluble film-forming polymer in the form of particles dispersed in the aqueous medium.

32. An assembly according to claim 24, wherein said nail varnish or nail care product further comprises a water-insoluble film-forming polymer in the form of particles dispersed in the aqueous medium.

33. An application assembly for a nail varnish or nail care product according to claim 24, wherein said bristles of said tuft are approximately parallel, and wherein said bristles are fastened to a free end of said wand.

34. A method of coating bristles of a brush according to claim 11, wherein said bristles of said tuft are approximately parallel, and wherein said bristles are fastened to a free end of said wand.

35. A brush according to claim 1, wherein said bristles of said tuft are approximately parallel, and wherein said bristles are fastened to a free end of said wand.

* * * * *

UNITED STATES PATENT AND TRADEMARK OFFICE
CERTIFICATE OF CORRECTION

PATENT NO.    : 6,210,059 B1
DATED         : April 3, 2001
INVENTOR(S)   : Ramin et al.

It is certified that error appears in the above-identified patent and that said Letters Patent is hereby corrected as shown below:

Claim 7,
Line 56, please change "40/100 of a millimeter" to -- 40/100 of a millimeter --.

Signed and Sealed this

Thirtieth Day of October, 2001

Attest:

NICHOLAS P. GODICI
Attesting Officer
Acting Director of the United States Patent and Trademark Office